United States Patent [19]

Schneiderman

[11] Patent Number: 4,567,065
[45] Date of Patent: Jan. 28, 1986

[54] DISPENSER GLOVES AND STOCKINETTS AND METHODS OF MANUFACTURING SAME

[76] Inventor: Charles I. Schneiderman, 10021 Sorrel Ave., Potomac, Md. 20854

[21] Appl. No.: 459,704

[22] Filed: Jan. 21, 1983

Related U.S. Application Data

[63] Continuation-in-part of Ser. No. 265,249, May 19, 1981, abandoned.

[51] Int. Cl.$^4$ ............... A61M 7/00; A61M 31/00; B05D 7/22
[52] U.S. Cl. .................................. 427/230; 53/429; 604/292
[58] Field of Search ................ 604/292; 427/230; 53/429

[56] References Cited

U.S. PATENT DOCUMENTS

| 3,384,083 | 5/1968 | Cozza et al. | 604/292 |
| 3,499,446 | 3/1970 | Tsuneizumi et al. | 604/292 |
| 4,059,097 | 11/1977 | Casey | 604/292 X |

*Primary Examiner*—Michael R. Lusignan
*Attorney, Agent, or Firm*—Wigman & Cohen

[57] ABSTRACT

An improved apparatus for dispensing lubricants, moisturizers and other medicinal agents to various parts of the body is disclosed. A glove or stockinett which contains such medicinal agent is utilized to cover the affected portion of the body in a safe and simple manner. Neither the dispensing glove nor stockinett require additional structure to affect the containment of the treating agent. The dispenser glove and stockinetts may be packaged in long rolls, either perforated or unperforated, or may be folded individually and packaged in a sterilized or non-sterilized environment. Methods of filling the dispensers, as well as a leak-resistant packaging method are also disclosed.

10 Claims, 19 Drawing Figures

DISPENSER GLOVES AND STOCKINETTS AND METHODS OF MANUFACTURING SAME

CROSS-REFERENCE TO RELATED APPLICATION

This application is a continuation-in-part of Ser. No. 265,249, filed May 19, 1981, now abandoned.

BACKGROUND OF THE INVENTION

The present invention relates generally to cosmetic and medicinal applicators and, more specifically, to hand and other body part applicators for medicinal type agents or ointments and methods of manufacturing these applicators.

Hands and other body appendages of persons readily become chapped and/or react to exposure in adverse environments and therefore require the application of lubricating, moisturizing or medicinal type agents from time to time. Usually, these types of agents are applied to the hands or body appendages when needed, incurring a great inconvenience to the person to whom these agents have been applied. Firstly, these agents must be applied and rubbed into the affected area for a period of time in order to result in the desired absorption necessary to treat the affected areas. Secondly, the application of such agents leaves the appendages with a thin coating of the agent which readily contaminates many materials contacted by the appendage in daily living.

Many different approaches have been used in the past to provide the user with a device for treating appendages of the body. In U.S. Pat. No. 2,601,851, to Jones, an applicator for treating skin ailments is disclosed which utilizes a bag-like envelope for the feet specifically for the application of medication to treat ringworm or athlete's foot. The device requires breaking of an inner envelope containing the medication by exerting pressure on the foot bag envelope.

Another approach is shown in U.S. Pat. No. 2,916,036 to Sutton, which discloses rubber gloves having an elaborate composition of layers or holding areas containing globules therein such that the warmth of the hand to which the gloves are applied may allow some lanolin to escape down the fibers of the glove to the skin of the user.

Cahill, U.S. Pat. No. 3,116,732, discloses a disposable hand care glove comprising an outer layer of leak-proof material, an inner layer of porous material and a plurality of reservoirs for containing a hand-treatment medication. In order to use this device, the reservoirs must be ruptured.

Still another approach is shown by Charos, U.S. Pat. No. 3,342,182. This patent discloses a packaged cream applicator glove which fits tightly around a person's wrist, has inner and outer portions, and a plurality of cartridges for holding the cream which extend through slots in one of the outer panel portions. Again, pressure must be placed over the cartridges in order to massage the cosmetic preparation into the skin of the hand.

In contrast to the prior art, the instant invention does not require any complex structure, any special handling or application techniques, nor the rupturing of any portions of the instant dispenser. The dispenser aspect of the instant invention is directed to a simple and inexpensive device which contains the treating agent therein.

Various methods are also known by which these prior art gloves are provided with various treatment medications. For example, U.S. Pat. No. 3,384,083 to Cozza et al, discloses a plastic glove manufactured from a continuous length of heat sealable fiber upon which a medicant is sprayed by a printing device. A second layer of heat sealable film is superimposed over the first layer, in order to form an article of apparel. This article, however, has medicant applied to one inside surface thereof.

In contrast to the prior art, the manufacturing aspect of the instant invention is directed to processes by which dispensers formed from a single layer of material have their entire inside surfaces coated with medication.

SUMMARY AND OBJECTS OF THE INVENTION

In view of the foregoing, it should be apparent that there still exists a need in the art for apparatus which can be readily used to apply a lubricating, moisturizing or medicinal type agent to the hand or other part of the body in a quick, clean and efficient manner and a method of manufacturing same. It is, therefore, a primary object of the present invention to provide apparatus for delivering a lubricating, moisturizing or medicinal type agent to the hand or other part of the body which is characterized by a glove which has been previously provided with the agent to be applied.

More particularly, it is an object of this invention to provide apparatus which will deliver a lubricating, moisturizing or medicinal type agent to the hand or other part of the body for an extended period of time.

Still more particularly, it is an object of this invention to provide a simple apparatus for applying lubricating, moisturizing or medicinal agents to parts of the human body such that the user may go about his daily routine without being concerned about contaminating materials touched by the portion of the body being treated.

Another object of the present invention is to provide an efficient and inexpensive means for applying lubricating, moisturizing or medicinal type agent to a desired part of the body in a simple manner.

A further object of the present invention is to provide apparatus which utilizes the heat of the area of the body being treated to enhance the absorption of the lubricant, moisturizer or medicinal agent being applied to the affected area. This confines the treating agent to the treated part, and, therefore, decreases any losses to evaporation or juxtaposed garments, bed sheets, work apparel, etc., as compared to the mere application of the treating agent to the affected part of the body.

Another object of the present invention is to utilize a manufacturing process for placing the medication or moisturizer in the dispensers in such a manner that the entire inside surface of the dispenser is coated with the medication or moisturizer.

Still another object of the present invention is to provide a method of packaging the medication-filled dispensers to extend their shelf-life by placing them in inexpensive leak-resistant containers.

Briefly described, these and other objects of the invention are accomplished in accordance with its dispenser aspects, by providing a glove or stockinett which already contains the treating agent. The glove or stockinett is then placed over the affected portion of the body and the treatment process begun. The gloves or stockinetts may contain a lubricating, moisturizing or medicinal type agent to be applied to the body. The glove or stockinett may be supplied for use by the user in either a continuous roll or as individually folded gloves or stockinetts packaged in a flat or folded individual configuration. Each glove or stockinett may be separately wrapped, non-sterilized or sterilized, and is preferably formed from a vinyl-latex material.

The manufacturing process aspects of the present invention are accomplished by providing a hollow form in the shape of a desired body part with a plurality of millipore openings. The dispenser is placed over the form and the moisturizer or medicinal agent with which the form has previously been filled, is forced out the millipores and onto the interior surfaces of the dispenser.

Alternately, a similarly shaped hollow form but without openings may be used to introduce the treating agent into the dispensers. This form is first placed into a container holding the treating agent and then placed inside of the dispenser, this distributing the treating agent throughout the dispenser.

Another aspect of the manufacturing process involves the packaging of the completed dispensers in a container such that the usefulness of the treating agent is preserved for an extended period of time. The applicators are folded over at their openings placed in a package of the same dimensions as the folded dispensers and then sealed. This serves to extend the shelf-life of the applicators.

With these and other objects, advantages and features of the invention that may become hereinafter apparent, the nature of the invention may be more clearly understood by reference to the following detailed description of the invention, the appended claims and to the several drawings attached herein.

DETAILED DESCRIPTION OF THE PREFERRED EMBODIMENT

Figure 1:
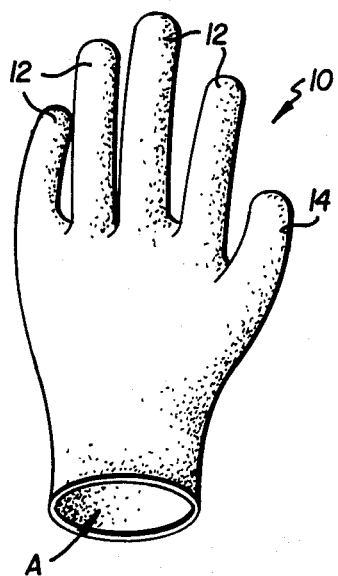
FIG. 1 is a drawing of the glove dispenser of the present invention.

Referring now in detail to the drawings wherein like parts are designated by like reference numerals throughout, there is illustrated in FIG. 1 a dispenser glove 10 of the present invention having four fingers 12 and a thumb 14. This glove has a hollow lumen into which a medicinal type agent, lubricant or moisturizer may be placed prior to packaging. The glove is preferably of the single layer or thickness vinyl-latex type, and may be reversible. Examples of agents which may be placed therein are: an anti-chapping agent, especially of the glycerin, oil or vaseline type of lubricant; and a moisturizer. When placed on the hands, this glove will deliver the lubricating/moisturizing agent to the hands by contact either for an overnight period or for a shorter wearing time. This treatment acts to reduce the chapped hands of the user. This glove may also contain any other medicinal type agent, either prescription or non-prescription, especially of the ointment, cream or lotion varieties, for the purpose of delivering these agents in the same manner as that discussed immediately above. Examples of this type of medicinal agent are: arthritis medicine and the accompanying warmth thereof; moisturizers; topical antibiotics; and burn medicine.

The glove 10 may also be manufactured in a mitten configuration (not shown) for accomplishing the very same purposes as described hereinabove.

Figure 2:
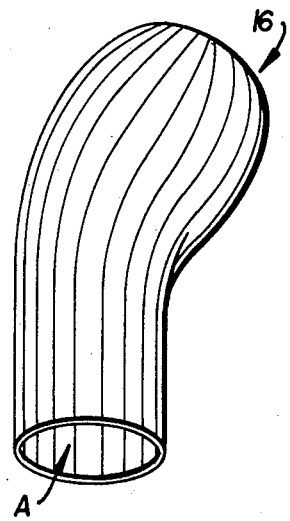
FIG. 2 is a drawing of a closed curved stockinett dispenser of the present invention.

FIG. 2 discloses a curved closed stockinett having one open and one closed end. The medicinal agent contained in the stockinett is placed in the hollow lumen of the stockinett at A.

Figure 3:
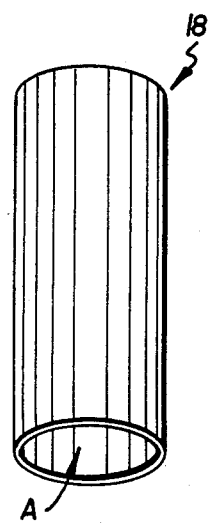
FIG. 3 is a drawing of a straight stockinett applicator of the present invention.

FIG. 3 discloses an open-ended straight stockinett 18 having both ends open. The medicinal agent to be contained in the stockinett is again placed in the hollow lumen designated as A.

The stockinetts as shown in FIGS. 2 and 3 may be either straight or curved, open at both ends or open at one end, and they may be in the form of a glove or a mitten, with or without fingers. They may contain a medicinal or lubricating or moisturizing agent and will allow said agent to spread all over the covered area of the body. By contact and warmth, the medicinal agent will soothe or aid the covered part of the body. The stockinetts may be manufactured from a single layer of thickness of a cotton-like or a latex-like or any other suitable material, and may be either separately wrapped, sterilized or non-sterilized. The stockinetts, especially of the cotton-synthetic fabric type, may be used to cover any of the body parts, limbs, trunk, head, etc. and contain any type of medicinal agent, prescription or non-prescription, and especially may contain ointment, creams, or lotions of the varieties as described in connection with the dispenser gloves 10.

FIG. 4 shows various methods of dispensing the dispenser gloves and/or dispenser stockinetts of the present invention.

Figure 4A:
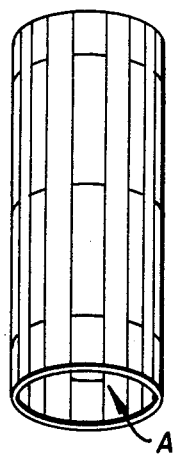
FIG. 4A is a drawing showing a continuous perforated long roll of the dispensers of the present invention.

FIG. 4A illustrates a long unperforated rolled long roll.

Figure 4B:
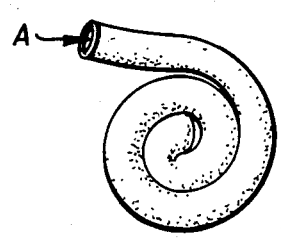
FIG. 4B is a drawing showing a rolled long roll of the dispensers of the present invention.

FIG. 4B illustrates an unperforated rolled long roll.

Figure 4C:
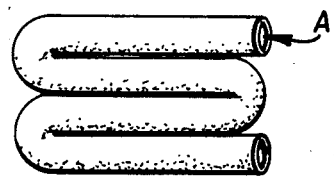
FIG. 4C is a drawing showing a folded long roll of the dispensers of the present invention.

FIG. 4C illustrates a folded long roll of the dispensers of the present invention. Each of these dispensers has a hollow lumen, shown at A, into which the medicinal type agent, lubricant or moisturizer is inserted prior to packaging. Although not specifically shown, any of the long rolls may be perforated or unperforated, rolled or folded or may be pre-cut of the same or variable lengths and widths. In addition, the dispenser gloves and stockinetts of the present invention may also be stretchable.

Figure 5A:
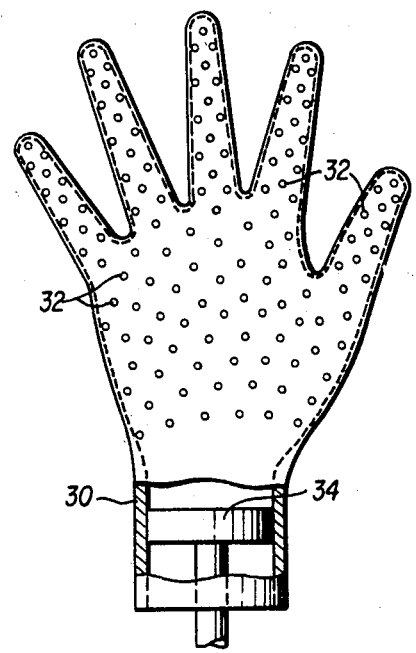
FIGS. 5A-D are a series of drawings depicting the filling of the dispenser glove of FIG. 1 with a treating agent using a hollow form having millipores.

FIGS. 5A-D illustrate a manufacturing process by which the dispenser glove shown, for example, in FIG. 1 may be filled with a medicating or treating agent. FIG. 5A shows a hollow form 30 shaped in a glove configuration and having a plurality of millipores 32 spaced thereon. These millipores are spaced such that when the dispenser glove 10 is placed on the form 30, the entire inside surface of the glove 10 is coated with the medicating agent. It is to be understood that the hollow form 30 may be constructed from any suitable material, such as metal or plastic and may be in any desired shape corresponding to the shape of the dispenser to be filled.

The hollow form 30 is provided with means (not shown) for filling the interior thereof with the treating agent and a piston 34 or other suitable mechanical, hydraulic, pneumatic or electrical means for forcing the treating agent of the form 30 through the millipores 32 and into the interior of the dispenser glove 10.

Figure 5B:
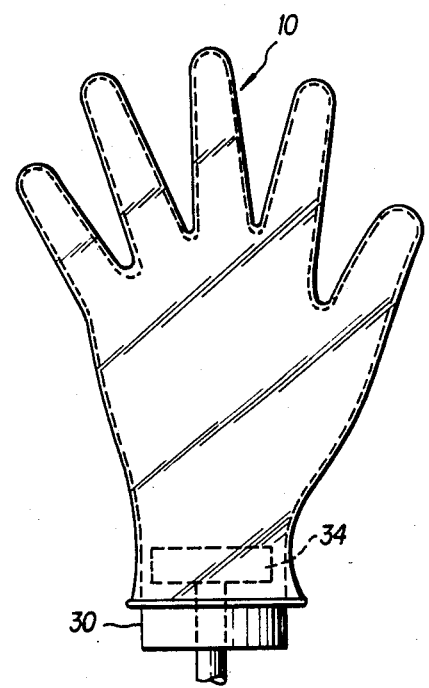
Figure 5C:
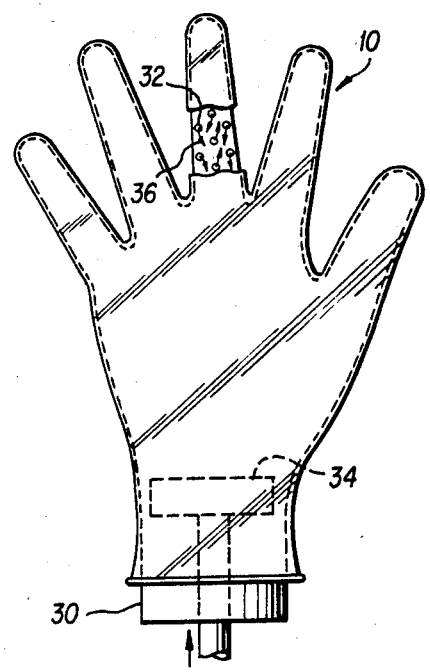
Figure 5D:
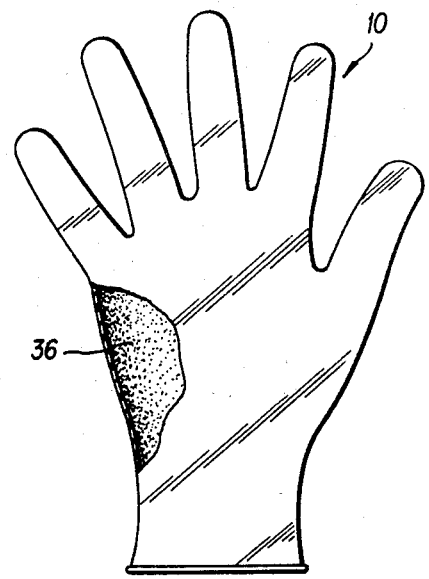

FIG. 5B shows the dispenser glove 10 in place on the form 30, which has been filled with treating agent. The dispenser glove or stockinett may either be mechanically or manually placed over and removed from the form 30. Alternatively, the dispenser may be made directly on the form 30, injected with the treating agent 36, and then removed for packaging. FIG. 5C shows the dispenser glove 10 still in place on the form 30, but with the treating agent 36 now coating the interior surfaces of the glove 10. FIG. 5D shows the dispenser glove 10 removed from the form 30 and having the medicinal agent 36 distributed throughout the inside surface thereof.

Figure 6A:
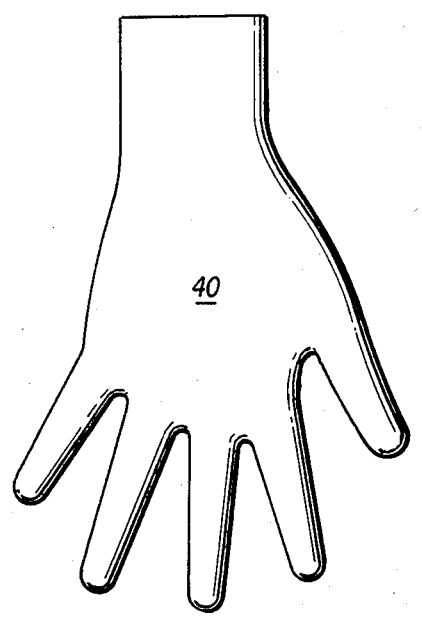
FIGS. 6A-E are a series of drawings depicting the filling of the dispenser glove of FIG. 1 with a treating agent using a hollow form without millipores.

FIGS. 6A-E illustrate an alternate manufacturing process by which the dispenser gloves 10 of FIG. 1 may be filled with a medicating agent. FIG. 6A shows a solid form 40 (which, of course, may also be hollow) without any openings. This form 40 may be shaped in a similar manner as form 32 described hereinabove.

Figure 6B:
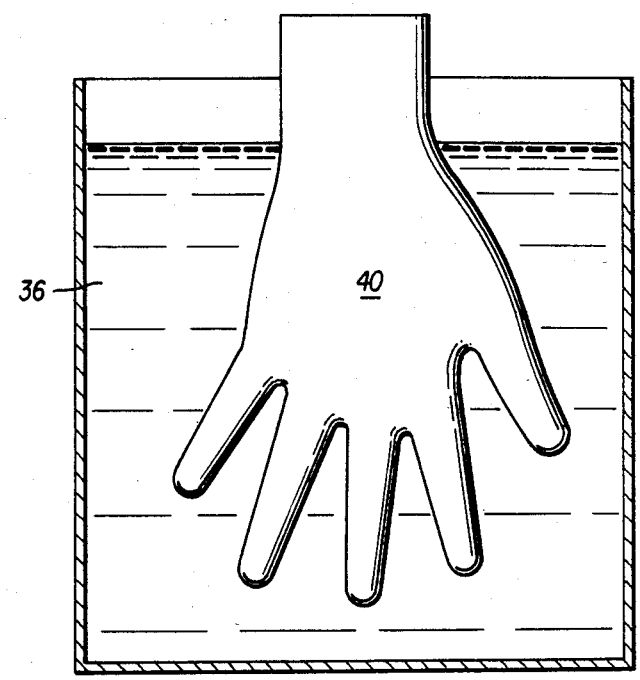
Figure 6C:
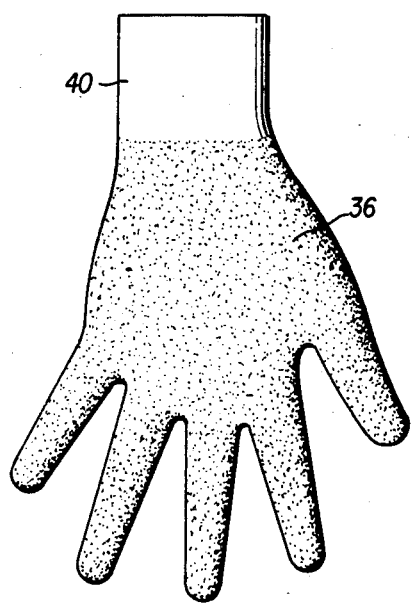
Figure 6D:
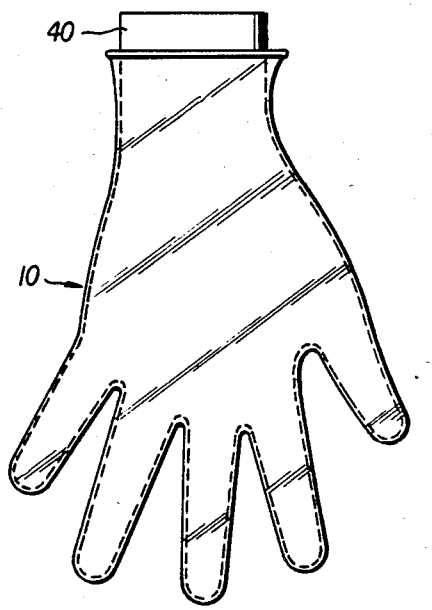
Figure 6E:
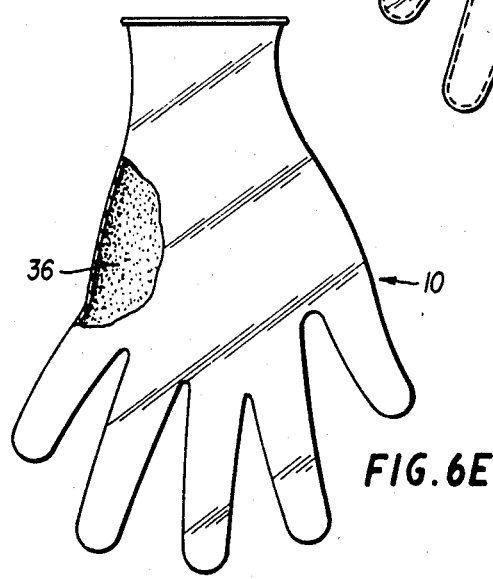

The form 40, as shown in FIG. 6B, is then placed into a container 42 of medicating agent 36 such that, as shown in FIG. 6C, when removed, the treating agent 36 is retained on the outside surface of the form 40. This may be accomplished by, for example, an electrostatic process. The medicating agent coated form 40 is then either mechanically or manually placed inside a dispensing glove 10, or other dispensing shape as previously described. As shown in FIG. 6D, in this configuration, the medicating agent 36 is distributed throughout the inside surfaces of the dispenser glove 10. FIG. 6E shows the completed dispenser glove 10 containing the medicated agent 36 coating its inside surfaces.

Figure 7A:
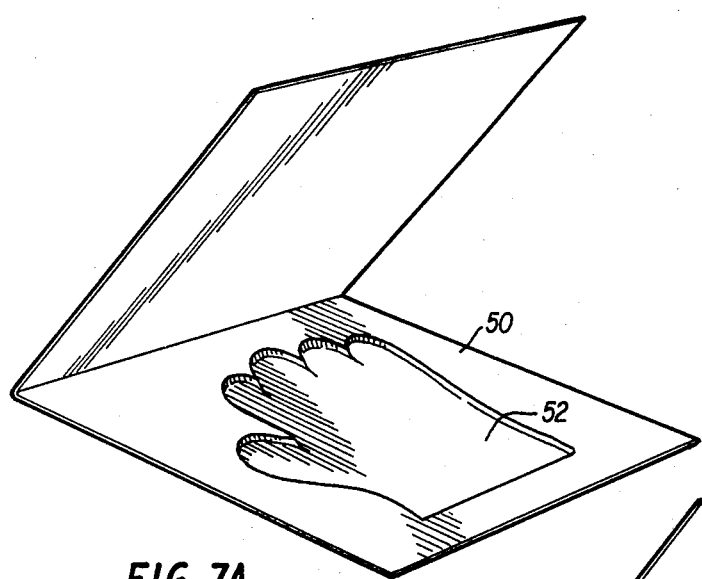
FIGS. 7A-D are a series of drawings depicting the packing of the dispenser glove of FIG. 1 in such a manner to provide an extended shelf life.

FIGS. 7A-D illustrate a method of packaging the dispenser gloves 10 (or other shapes) in order to provide for an extended shelf-life and usefulness of the medicating effects of the present invention. As shown in FIG. 7A, the packaging 50 is comprised of a foil wrapper having a hollow portion 52 corresponding to the shape of the dispenser to be packaged, except that the hollow portion is somewhat shorter at the open end of the dispenser. For example, as shown in FIG. 7A, the hollow portion 52 may be one inch shorter in the wrist area.

Figure 7B:
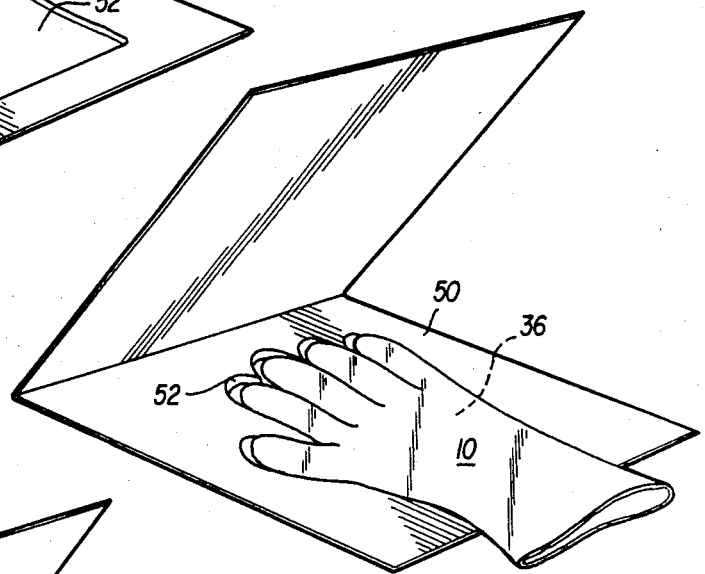
Figure 7C:
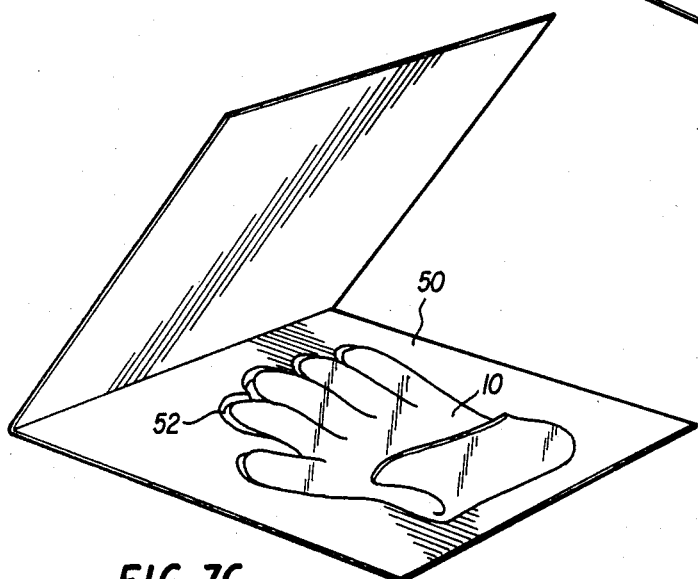
Figure 7D:
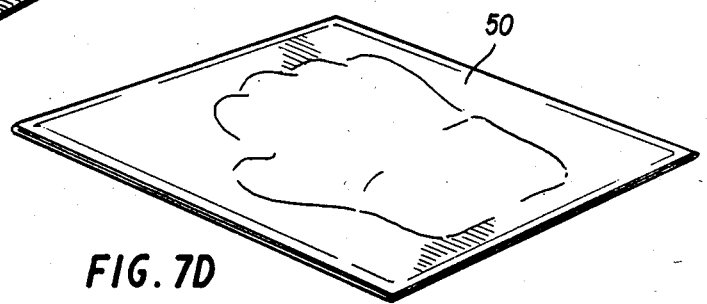

As shown in FIG. 7B, the dispenser glove 10 containing the medicating agent 36 is placed in the hollow portion 52. The part of the glove 10 which extends past the end of the hollow portion 52 is folded over, as shown by B in FIG. 7C. In FIG. 7D, the package 50 has been closed and hermetically sealed and is leak-resistant. It should be understood that, instead of a foil-type hermetically or thermally sealable wrapper, package 50 may be comprised of a plastic type ziplock bag or a disposable plastic box with a shut-tight latch lid. Obviously, the packaging 50 is designed to be shorter than the dispenser to be packaged therein, in order to facilitate the folding operation.

The packaging steps described above may be accomplished either mechanically or manually, as desired.

Any of the dispensers of the present invention may be either individually packaged and wrapped or may be boxed collectively in a single container such as pop-up pre-medicated gloves in a box. The dispensers may be of one or varied sizes.

There has thus been disclosed a simple, yet effective, dispenser for containing lubricating, moisturizing or other medicinal agents for application to parts of the body. No additional structures need be contained in, on or accompany the dispenser gloves or stockinetts of the present invention. In addition, these dispensers may be utilized on non-human mammals and other animals.

Although only a preferred embodiment is specifically illustrated and described herein, it will be appreciated that many modifications and variations of the present invention are possible in light of the above teachings and within the purview of the appended claims without departing from the spirit and intended scope of the invention.

What is claimed is:

1. A method of filling a dispensing device for fitting around a portion of the user's body with a treating agent, comprising:
   placing said treating agent into a hollow form having a plurality of millipore openings;
   placing said dispensing device over said hollow form; and
   injecting said treating agent onto the interior surfaces of said dispensing device by forcing it through said plurality of millipore openings;
   whereby said treating agent is uniformly distributed throughout substantially the entire interior surfaces of said dispensing device.

2. The method of claim 1, wherein the shape of said form corresponds to the shape of said dispensing device.

3. The method of claim 1, wherein said dispensing device is in the shape of a glove.

4. The method of claim 1, wherein said dispensing device is in the shape of a stockinett.

5. The method of claim 1, wherein said treating agent is a lubricant.

6. The method of claim 1, wherein said treating agent is a moisturizer.

7. The method of claim 1, wherein said treating agent is one of a topical antibiotic, an arthritis medicine and a burn medicine.

8. The method of claim 1, wherein said treating agent is in the form of one of an ointment, a cream, and a lotion.

9. A method of manufacturing a dispensing device for applying a treating agent to a portion of a user's body, comprising:
   (a) providing a dispensing device adapted to fit over a portion of a user's body;
   (b) providing a hollow form having a plurality of millipore openings spaced thereon and shaped to conform to a portion of the user's body desired to be treated by said dispensing device;
   (c) placing said dispensing device over the hollow form;
   (d) supplying the treating agent to the inside of the hollow form; and
   (e) forcing the treating agent under pressure through said millipore openings to uniformly distribute the treating agent throughout substantially the entire interior surfaces of said treating device.

10. The method of claim 9, wherein said dispensing device is in the shape of a glove and the hollow form includes millipore openings positioned to distribute the treating agent between the fingers of the glove so as to facilitate treating cracks or the like between a user's fingers.

* * * * *